United States Patent
Bergmann et al.

(10) Patent No.: US 9,810,699 B2
(45) Date of Patent: *Nov. 7, 2017

(54) RISK ASSESSMENT FOR ANTIBIOTICS TREATMENT IN PATIENTS SUFFERING FROM PRIMARY NON-INFECTIOUS DISEASE BY DETERMINING THE LEVEL OF PROCALCITONIN

(71) Applicant: B.R.A.H.M.S GmbH, Henningsdorf (DE)

(72) Inventors: Andreas Bergmann, Berlin (DE); Joachim Struck, Berlin (DE)

(73) Assignee: B.R.A.H.M.S GMBH, Hennigsdorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/672,801

(22) Filed: Mar. 30, 2015

(65) Prior Publication Data

US 2015/0247871 A1   Sep. 3, 2015

Related U.S. Application Data

(63) Continuation of application No. 13/264,252, filed as application No. PCT/EP2010/002279 on Apr. 14, 2010, now Pat. No. 9,046,532.

(30) Foreign Application Priority Data

Apr. 14, 2009 (EP) .................................... 09157886

(51) Int. Cl.
G01N 33/74 (2006.01)

(52) U.S. Cl.
CPC ....... *G01N 33/74* (2013.01); *G01N 2333/585* (2013.01); *G01N 2800/32* (2013.01); *G01N 2800/325* (2013.01)

(58) Field of Classification Search
CPC ............. G01N 33/74; G01N 2333/585; G01N 2800/32; G01N 2800/325
See application file for complete search history.

(56) References Cited

U.S. PATENT DOCUMENTS

| 5,420,016 | A | 5/1995 | Boguslaski et al. |
| 6,451,311 | B2 | 9/2002 | Althaus et al. |
| 8,465,941 | B2 * | 6/2013 | Bergmann ............. G01N 33/74 435/15 |
| 2003/0119064 | A1 | 6/2003 | Valkirs et al. |
| 2008/0206797 | A1 | 8/2008 | Bergmann et al. |
| 2010/0047835 | A1 | 2/2010 | Bergmann et al. |
| 2011/0136161 | A1 | 6/2011 | Struck et al. |
| 2011/0152170 | A1 | 6/2011 | Struck et al. |

FOREIGN PATENT DOCUMENTS

| DE | 10 2006 046996 A1 | 4/2008 | |
| GB | WO 2008/040328 A2 * | 4/2008 | ............. G01N 33/53 |
| WO | 2006/071583 A2 | 7/2006 | |
| WO | 2009/019230 A2 | 2/2009 | |

OTHER PUBLICATIONS

Morgenthaler et al., Sensitive immunoluminometric Assay for the Detection of Procalcitonin, Clinical Chemistry, 48, No. 5, 2002, pp. 788-790.*

Christ-Cain, M., et al., "Effect of procalcitonin guided treatment on anibiotic use and outcome in lower respiratory tract infections: cluster-randomised, single-blinded intervention trial," The Lancet, Feb. 21, 2004, vol. 363, No. 9409, pp. 600-607; Cited in the International Search Report, dated Jun. 15, 2010, issued in corresponding PCT/EP2010/002279.

Sandek, A., et al., "Procalcitonin-guided antibiotic treatment in heart failure," The Lancet, May 8, 2004, vol. 363, No. 9420, p. 1555; Cited in the International Search Report, dated Jun. 15, 2010, issued in corresponding PCT/EP2010/002279.

International Search Report, dated Jun. 15, 2010, issued in corresponding PCT/EP2010/002279.

Written Opinion, dated Jun. 15, 2010, issued in corresponding PCT/EP2010/002279.

Haubitz et al., "Streamlining antibiotic therapy with procalcitonin protocols: consensus and controversies." Expert Review of Respiratory Medicine, Apr. 2013, vol. 7, No. 2, pp. 145-157.

Qedra et al., "Procalcitonin and modified Sofa Score the Best Predictors of Mortality after Heart and Lung Transplantation", The Journal of Heart and Lung Transplantation, 2004, vol. 23, No. 2S, p. S117.

Mattie et al., "Pharmacodynamics of antibiotics with respect to bacterial killing of and release of lipoteichoic acid by *Streptococcus pneumoniae*", Journal of Antimicrobial Chemotherapy, 2005, vol. 56, pp. 154-159.

* cited by examiner

*Primary Examiner* — Gary W Counts
(74) *Attorney, Agent, or Firm* — Millen White Zelano and Branigan, PC; John Sopp; Csaba Henter

(57) ABSTRACT

A diagnostic method for the identification of a subject suffering from a primary non-infectious disease having an increased risk of an adverse outcome potentially being induced by the administration of an antibiotic to said subject comprising the determination of the level of Procalcitonin (PCT) or a fragment thereof or a precursor or fragment thereof having a length of at least 12 amino acid residues in a sample of a bodily fluid from said subject and the correlation of the determined level to a potential risk induced by the administration of an antibiotic, as well as a kit for performing the method and methods of treatment based thereon.

17 Claims, 4 Drawing Sheets

Fig. 4

SEQ ID NO:1

```
1    APFRSALESS PADPATLSED EARLLLAALV QDYVQMKASE LEQEQEREGS
51   SLDSPRSKRC GNLSTCMLGT YTQDFNKFHT FPQTAIGVGA PGKKRDMSSD
101  LERDHRPHVS MPQNAN
```

RISK ASSESSMENT FOR ANTIBIOTICS TREATMENT IN PATIENTS SUFFERING FROM PRIMARY NON-INFECTIOUS DISEASE BY DETERMINING THE LEVEL OF PROCALCITONIN

REFERENCE TO SEQUENCE LISTING

This application contains a Sequence Listing submitted in electronic and print form. The electronic and print form of the Sequence Listing are identical to each other pursuant to 37 CFR §1.52(e)(4), contains the following file: "BOEHMERP0111.txt", having a size in bytes of 1.37 KB, recorded on Nov. 28, 2011. The information contained in the sequence listing is hereby incorporated by reference in its entirety pursuant to 37 CFR §1.52(e)(5).

FIELD OF THE INVENTION

The present invention is in the field of clinical diagnostics. Particularly the present invention relates to the risk assessment in patients suffering from a primary non-infectious disease by determination of the level of Procalcitonin (PCT) in a sample of a patient.

BACKGROUND OF THE INVENTION

Procalcitonin (PCT) is known to be a marker for bacterial infection and sepsis. High blood or serum levels of this peptide prohormone are indicators for severe infections.

In a clinical setting, patients with primary non-infectious diseases often are, as a precautionary measure, treated with antibiotics in order to prevent or treat potential infections which may or may not yet be manifested, independently of whether the presence of a bacterial infection has actually been diagnosed.

The present invention is based on the surprising finding of the inventors that the treatment of patients suffering from a primary non-infectious disease with an antibiotic in order to treat or prevent potential bacterial infections is in a particular group of patients associated with an increased risk of an adverse outcome. Particularly patients having a low blood PCT level are subject to an increased risk when subjected to antibiotics. It is according to the invention advisable to determine the PCT level in a sample of a bodily fluid from a patient suffering from a primary non-infectious disease before starting a potentially harmful antibiotic therapy. High blood or serum PCT levels indicate the presence of a severe bacterial infection or even sepsis and requires the treatment of the respective patient with antibiotics. However, patients suffering from a primary non-infectious disease are up to now not routinely screened for low PCT levels before starting an antibiotics therapy.

DESCRIPTION OF THE INVENTION

Thus, the present invention relates to a diagnostic method for the identification of a subject suffering from a primary non-infectious disease having an increased risk of an adverse outcome potentially being induced by the administration of an antibiotic to said subject, comprising the steps of:
(i) providing a sample of a bodily fluid from said subject suffering from a primary non-infectious disease,
(ii) determining in said sample the level of Procalcitonin (PCT) or a fragment thereof or a precursor or fragment thereof having a length of at least 12 amino acid residues,
(iii) correlating the determined level of Procalcitonin (PCT) or a fragment thereof or a precursor or fragment thereof having a length of at least 12 amino acid residues to a potential risk of having an adverse outcome induced by the administration of an antibiotic.

The diagnostic method of the invention is an in vitro method.

Said subject suffering from a primary non-infectious disease does not have a bacterial infection, especially does not have a severe bacterial infection, preferably does not exhibit any symptoms of a bacterial infection. The herein described methods according to the invention enable the prediction of an adverse outcome induced by antibiotics for a subject suffering from a primary non-infectious disease. Thus, the herein described methods according to the invention are equally methods of predicting an adverse outcome induced by antibiotics for a subject suffering from a primary non-infectious disease.

For the very first time it was found that a very low PCT level indicates an enhanced risk of attracting an adverse outcome for a subject suffering from a primary non-infectious disease when antibiotics are administered to said subject.

Thus, in a preferred embodiment if the determined level of Procalcitonin (PCT) or a fragment thereof or a precursor or fragment thereof having a length of at least 12 amino acid residues goes below a certain threshold it is predicted that said subject has an enhanced risk of having an adverse outcome when antibiotics are administered. In contrast thereto, according to the methods of the prior art it was known that below a certain threshold of PCT Procalcitonin (PCT) or a fragment thereof or a precursor or fragment thereof having a length of at least 12 amino acid residues the treatment with antibiotics may not be needed but it was not known that there is a correlation between the determined level of Procalcitonin (PCT) or a fragment thereof or a precursor or fragment thereof having a length of at least 12 amino acid residues and the enhanced risk of an adverse outcome induced by antibiotics treatment for said subjects.

According to the prior art suspected bacterial infections were often treated with antibiotics without evidence of clinically relevant bacterial disease. It was recommended to administer antibiotics only in case of having the evidence of a clinically relevant bacterial disease in order to save money, in order to avoid side effects or avoid the spread of antibiotic-resistant bacteria, It is a achievement of the present invention to predict the enhanced risk of having severe side-effects or having an adverse outcome induced by antibiotics by correlating a determined level of Procalcitonin (PCT) or a fragment thereof or a precursor or fragment thereof having a length of at least 12 amino acid residues to said risk.

Thus, the determination of the level of Procalcitonin (PCT) or a fragment thereof or a precursor or fragment thereof having a length of at least 12 amino acid residues before treatment of subjects suffering from a primary non-infectious disease with antibiotics is an absolutely unavoidable measure in order to identify those subjects which have an enhanced risk of having an adverse outcome induced by antibiotics.

Said outcome is preferably an adverse event. An adverse event is defined as an event compromising the health of an individual. Said adverse event is not restricted to but may be selected from the group comprising a coronary event, cardiovascular event, death, heart failure, diabetes, hypertension. Coronary events are defined as fatal or non-fatal acute coronary syndromes including myocardial infarction, or death due to ischemic heart disease. Cardiovascular events are defined as fatal or non-fatal acute coronary syndromes including myocardial infarction, fatal or non-fatal stroke, or death due to cardiovascular disease.

Said adverse outcome may be side-effects induced by antibiotics treatment, especially severe side effects induced antibiotics treatment. Such side effect may include such as upset stomach, diarrhea, and, in women, vaginal yeast infections. Some subjects may be allergic to antibiotics.

Said outcome or said risk may for instance regard the survival and/or a functional outcome.

The term "outcome" herein relates for instance to the survival of the patient after a defined time, e.g. after 3 days, 5 days, 10 days, 14 days, 20 days, 3 weeks, 4 weeks, 30 days, 45 days, 60 days, 90 days, 3 months, 6 months, 1 year, preferably 30 days.

The term "functional outcome" in the context of the present invention relates to the degree of severity of disease, i.e. the state of health of the patient after a defined time, e.g. 3 days, 5 days, 10 days, 14 days, 20 days, 3 weeks, 4 weeks, 30 days, 45 days, 60 days, 90 days, 3 months, 6 months, 1 year, preferably 30 days.

The adverse outcome may e.g. be mortality. This means that with the methods of the present invention, subjects can be identified for which the administration of antibiotics would lead to an increased risk of a fatal outcome within a given period, e.g. within 1, 2, 3, 4, 5, 6, 7, 8, 9, 10, 14, 15, 20, 21, 30, 60, or 90 days after start of the treatment with an antibiotic.

The primary non-infectious disease from which the subject suffers may preferably be selected from the group of cardiovascular disease, cardiac disease, cancer, a disease of the CNS, diabetes, autoimmune disorder, and disorder associated with inflammation.

Said primary disease may in a particular example be heart failure. The subjects may in a preferred embodiment suffer from heart failure and/or shortness of breath. Heart failure herein preferably relates to congestive heart failure (CHF). The heart failure may preferably be acute heart failure (AHF) or chronic heart failure.

Heart failure is a cardiac condition that occurs when a problem with the structure or function of the heart impairs its ability to supply sufficient blood flow to meet the body's needs. It can cause a large variety of symptoms, particularly shortness of breath and ankle swelling, but some patients can be completely symptom free. Heart failure is often undiagnosed due to a lack of a universally agreed definition and challenges in definitive diagnosis, particularly in early stage. With appropriate therapy, heart failure can be managed in the majority of patients, but it is a potentially life threatening condition, and progressive disease is associated with an annual mortality of 10%. It is the leading cause of hospitalization in people older than 65.

Shortness of breath (SoB; also known as dyspnea or difficulty breathing) relates to a sensation of difficult or uncomfortable breathing or a feeling of not getting enough air in a subject. SoB may have many different causes, among them heart diseases such as heart attack, congestive heart failure, and pulmonary hypertension.

In a particularly preferred embodiment of the present invention, the subject is suffering from shortness of breath and subsequently diagnosed with heart failure.

In the context of the present invention a concentration of PCT or a fragment thereof or a precursor or fragment thereof below 200 pg/mL, preferably below 150 pg/mL, more preferably below 100 pg/mL, most preferably below 50 pg/mL, in the sample correlates to an increased risk induced by the potential administration of an antibiotic.

These values have been determined with a PCT test format (BRAHMS KRYPTOR PCT sensitive), which has the same calibration in the quantitative measuring range as a more sensitive PCT Assay (BRAHMS PCT LIA sensitive), the latter being able to quantitatively determine PCT levels in the normal population, giving median PCT levels as described in EP 09011073.5 ("Procalcitonin for the prognosis of adverse events in the asymptomatic population"). The above mentioned values might be different in other PCT assays, if these have been calibrated differently from BRAHMS KRYPTOR PCT sensitive. The above mentioned values shall apply for such differently calibrated PCT assays accordingly, taking into account the differences in calibration. One possibility of quantifying the difference in calibration is a method comparison analysis (correlation) of the PCT assay in question with the BRAHMS KRYPTOR PCT sensitive by measuring PCT in samples using both methods. Another possibility is to determine with the PCT assay in question, given this test has sufficient analytical sensitivity, the median PCT level of a representative normal population, compare results with the median PCT levels as described in EP 09011073.5 ("Procalcitonin for the prognosis of adverse events in the asymptomatic population") and recalculate the calibration based on the difference obtained by this comparison.

In a particular embodiment, additionally at least one clinical parameter is determined selected from the group comprising: age, gender, systolic blood pressure, diastolic blood pressure, antihypertensive treatment, history of stroke, wheezing, body mass index, heart rate, temperature, presence of diabetes mellitus and current smoking habits, most preferably selected from the group consisting of heart rate, temperature, body mass index, systolic blood pressure and diastolic blood pressure.

In some particular embodiments other laboratory parameters may additionally be determined, e.g. the level of neutrophil granulocyte or the level of further prognostic markers, particularly other peptide hormones and fragments thereof or precursors or fragments thereof.

The term "sample" as used herein refers to a sample of bodily fluid obtained for the purpose of diagnosis, prognosis, or evaluation of a subject of interest, such as a patient. Preferred test samples include blood, serum, plasma, cerebrospinal fluid, urine, saliva, sputum, and pleural effusions. In addition, one of skill in the art would realize that some test samples would be more readily analyzed following a fractionation or purification procedure, for example, separation of whole blood into serum or plasma components.

Thus, in a preferred embodiment of the invention the sample is selected from the group consisting of a blood sample, a serum sample, a plasma sample, a cerebrospinal fluid sample, a saliva sample and a urine sample or an extract of any of the aforementioned samples. Preferably, the sample is a blood sample, most preferably a serum sample or a plasma sample.

The term "subject" as used herein refers to a living human or non-human organism, preferably a patient that is receiving medical care or that should receive medical care due to a primary non-infectious disease. This includes persons with no defined illness who are being investigated for signs of pathology. Thus, the methods and assays described herein are applicable to both human and veterinary disease.

"Fragments" of PCT or precursors thereof relate to fragments of at least twelve amino acid residues in length.

PCT in the context of the present invention preferably relates to a peptide spanning the amino acid residues 1-116, 2-116, or 3-116 or fragments thereof. Procalcitonin may comprise posttranslational modifications such as glycosylation, liposidation or derivatisation. PCT itself is a precursor of calcitonin and katacalcin. The amino acid sequence of PCT is given in SEQ ID NO:1 (FIG. 4).

The term "level" in the context of the present invention relates to the concentration (preferably expressed as weight/volume; w/v) of PCT (or a fragment/precursor) in the sample taken from the subject.

Determining (or measuring or detecting) the level of PCT or a fragment or a precursor or fragment thereof herein is performed using a detection method and/or a diagnostic assay as explained below.

As mentioned herein, an "assay" or "diagnostic assay" can be of any type applied in the field of diagnostics. Such an assay may be based on the binding of an analyte to be detected to one or more capture probes (capture molecules) with a certain affinity. Concerning the interaction between capture molecules and target molecules or molecules of interest, the affinity constant is preferably greater than $10^8$ $M^{-1}$.

In the context of the present invention, "capture molecules" are molecules which may be used to bind target molecules or molecules of interest, i.e. analytes (i.e. in the context of the present invention the cardiovascular peptide(s)), from a sample. Capture molecules must thus be shaped adequately, both spatially and in terms of surface features, such as surface charge, hydrophobicity, hydrophilicity, presence or absence of lewis donors and/or acceptors, to specifically bind the target molecules or molecules of interest. Hereby, the binding may for instance be mediated by ionic, van-der-Waals, pi-pi, sigma-pi, hydrophobic or hydrogen bond interactions or a combination of two or more of the aforementioned interactions between the capture molecules and the target molecules or molecules of interest. In the context of the present invention, capture molecules may for instance be selected from the group comprising a nucleic acid molecule, a carbohydrate molecule, a RNA molecule, a protein, an antibody, a peptide or a glycoprotein. Preferably, the capture molecules are antibodies, including fragments thereof with sufficient affinity to a target or molecule of interest, and including recombinant antibodies or recombinant antibody fragments, as well as chemically and/or biochemically modified derivatives of said antibodies or fragments derived from the variant chain with a length of at least 12 amino acids thereof.

The preferred detection methods comprise immunoassays in various formats such as for instance radioimmunoassay (RIA), chemiluminescence- and fluorescence-immunoassays, Enzyme-linked immunoassays (ELISA), Luminex-based bead arrays, protein microarray assays, and rapid test formats such as for instance immunochromatographic strip tests.

The assays can be homogenous or heterogeneous assays, competitive and non-competitive sandwich assays. In a particularly preferred embodiment, the assay is in the form of a sandwich assay, which is a non-competitive immunoassay, wherein the molecule to be detected and/or quantified is bound to a first antibody and to a second antibody. The first antibody may be bound to a solid phase, e.g. a bead, a surface of a well or other container, a chip or a strip, and the second antibody is an antibody which is labeled, e.g. with a dye, with a radioisotope, or a reactive or catalytically active moiety. The amount of labeled antibody bound to the analyte is then measured by an appropriate method. The general composition and procedures involved with "sandwich assays" are well-established and known to the skilled person. (*The Immunoassay Handbook*, Ed. David Wild, Elsevier LTD, Oxford; 3rd ed. (May 2005), ISBN-13: 978-0080445267; Hultschig C et al., Curr Opin Chem Biol. 2006 February; 10(1):4-10. *PMID:* 16376134), incorporated herein by reference).

In a particularly preferred embodiment the assay comprises two capture molecules, preferably antibodies which are both present as dispersions in a liquid reaction mixture, wherein a first labeling component is attached to the first capture molecule, wherein said first labeling component is part of a labeling system based on fluorescence- or chemiluminescence-quenching or amplification, and a second labeling component of said marking system is attached to the second capture molecule, so that upon binding of both capture molecules to the analyte a measurable signal is generated that allows for the detection of the formed sandwich complexes in the solution comprising the sample.

Even more preferred, said labeling system comprises rare earth cryptates or rare earth chelates in combination with a fluorescence dye or chemiluminescence dye, in particular a dye of the cyanine type.

In the context of the present invention, fluorescence based assays comprise the use of dyes, which may for instance be selected from the group comprising FAM (5- or 6-carboxyfluorescein), VIC, NED, Fluorescein, Fluoresceinisothiocyanate (FITC), IRD-700/800, Cyanine dyes, such as CY3, CY5, CY3.5, CY5.5, Cy7, Xanthen, 6-Carboxy-2',4',7',4,7-hexachlorofluorescein (HEX), TET, 6-Carboxy-4',5'-dichloro-2',7'-dimethodyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), Rhodamine, Rhodamine Green, Rhodamine Red, Rhodamine 110, BODIPY dyes, such as BODIPY TMR, Oregon Green, Coumarines such as Umbelliferone, Benzimides, such as Hoechst 33258; Phenanthridines, such as Texas Red, Yakima Yellow, Alexa Fluor, PET, Ethidiumbromide, Acridinium dyes, Carbazol dyes, Phenoxazine dyes, Porphyrine dyes, Polymethin dyes, and the like.

In the context of the present invention, chemiluminescence based assays comprise the use of dyes, based on the physical principles described for chemiluminescent materials in Kirk-Othmer, Encyclopedia of chemical technology, $4^{th}$ ed., executive editor, J. I. Kroschwitz; editor, M. Howe-Grant, John Wiley & Sons, 1993, vol. 15, p. 518-562, incorporated herein by reference, including citations on pages 551-562. Preferred chemiluminescent dyes are acridiniumesters.

The present invention also relates to the use of a method according to the invention for the stratification of subjects suffering from a primary non-infectious disease into a group of subjects having an increased risk of an adverse outcome induced by the administration of an antibiotic and a group of subjects having no risk induced by the administration of an antibiotic.

Furthermore, the invention pertains to the use of a kit comprising one or more antibodies directed against PCT or a fragment thereof or a precursor or fragment thereof for the stratification of subjects suffering from a primary non-infectious disease into a group of subjects having an increased risk of an adverse outcome induced by the administration of an antibiotic and a group of subjects having no risk induced by the administration of an antibiotic.
Sequences

```
SEQ ID NO: 1 (amino acid sequence of PCT):
  1 APFRSALESS PADPATLSED EARLLLAALV QDYVQMKASE LEQEQEREGS

51 SLDSPRSKRC GNLSTCMLGT YTQDFNKFHT FPQTAIGVGA PGKKRDMSSD

101 LERDHRPHVS MPQNAN
```

DESCRIPTION OF DRAWINGS

FIGS. 2A-D illustrates the survival (in %) of the patients diagnosed with AHF in the study of example 1 over time (in weeks) up to 90 days from admission. Solid lines regard the group of patients that have not received antibiotics treatment, while the dashed lines concern patients treated with antibiotics. FIG. 2A: all patients diagnosed with AHF (n=561), antibiotics treated: n=104 (18 dead after 90 days), non-antibiotics-treated: n=457 (46 dead after 90 days), p=0.03011; FIG. 2B: patients diagnosed with AHF and having plasma PCT levels of from 20.7 to 51.1 pg/mL (n=112), antibiotics treated: n=17 (4 dead after 90 days), non-antibiotics-treated: n=95 (5 dead after 90 days), p=0.00632; FIG. 2C: patients diagnosed with AHF and having plasma PCT levels of from 51.1 to 205 pg/mL (n=336), antibiotics treated: n=55 (9 dead after 90 days), non-antibiotics-treated: n=281 (24 dead after 90 days), p=0.06328; FIG. 2D: patients diagnosed with AHF and having plasma PCT levels of from 205 to 230 pg/mL (n=113), antibiotics treated: n=32 (5 dead after 90 days), non-antibiotics-treated: n=81 (17 dead after 90 days), p=0.06328.

FIGS. 3A-D illustrates the survival (in %) of the patients diagnosed with AHF in the study of example 1 over time (in days) up to 90 days from admission. Solid lines regard the group of patients that have not received antibiotics treatment, while the dotted lines concern patients treated with antibiotics. FIGS. 3A-D correspond to the same patient groups as in FIG. 2A-D, respectively. The data of FIG. 3 has been adjusted for the occurrence of wheezing, history of stroke and blood level of neutrophil granulocytes in the patients to account for possible differences between the antibiotic treated group and the non-treated group.

FIG. 4: Amino acid sequence of Procalcitonin (PCT), SEQ ID NO: 1

EXAMPLES

Example 1: Clinical Study

15 Enrolling Centers—Recruiting 1641 Patients with Shortness of Breath (SoB) and Acute Heart Failure (AHF)

This study was approved by the institutional review boards of 8 institutions. 1,641 patients from fifteen centers were enrolled from March 2007 to February 2008 that included 8 United States, 6 European and 1 New Zealand center. To be eligible patients had to report shortness of breath as their primary complaint upon presentation to the emergency department. Patients under 18 years of age or unable to provide consent were excluded. Patients with an acute ST-elevation myocardial infarction or on hemodialysis were also excluded. Antibiotics were given to some of the patients at the assessment of the treating physician.

For each patient enrolled in the study, the emergency physician, blinded to investigational marker results, assessed the probability that the patient had acute HF or pneumonia via two separate Likert scale questionnaires, assigning a value of 0 to 100 percent clinical certainty.

Summary of Study Particulars:
- Patients included who presented to emergency department (ED) with SoB not from trauma, or obvious myocardial infarction (MI), and not on dialysis.
- After consenting, MD assessment of probability of heart failure and/or pneumonia.
- Two independent cardiologists agreed on final diagnosis following discharge.
- Follow-up for 90 days for survival; Outcome "All cause mortality within 90 days".

Figure 1:
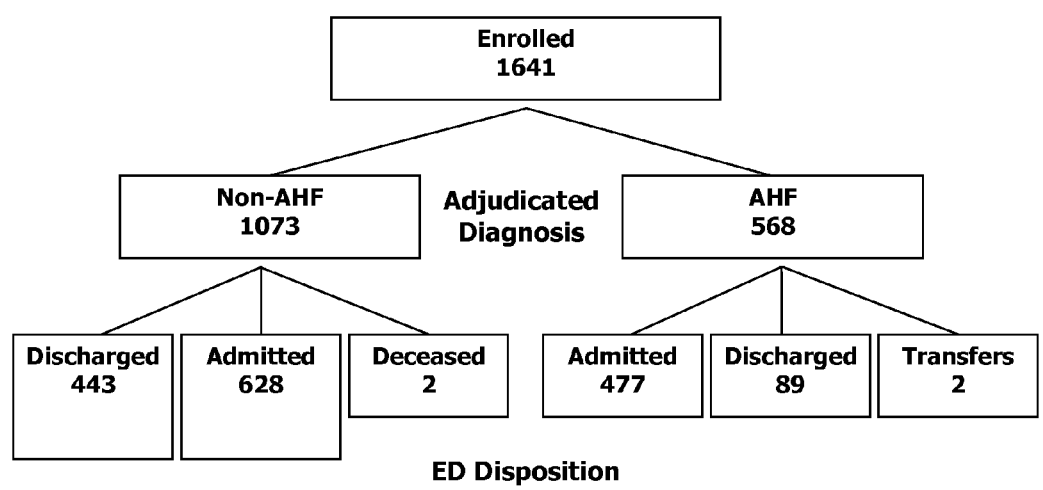
FIG. 1: Summary of patients in the clinical study of example 1.

Table 1 and FIG. 1 further summarize details on the patients in the study.

Confirmation of Diagnosis

To determine the gold standard diagnosis, two cardiologists independently reviewed all medical records pertaining to the patient and independently classified the diagnosis as dyspnea due to heart failure, pneumonia or due to other underlying cause. Both cardiologists were blinded to each others assessments, the investigational markers, and the emergency physician's preliminary diagnosis. They had access to the ED case report forms that included medical history plus data on chest radiography, radionuclide angiography, echocardiography, and cardiac catheterization as available, as well as the hospital course for those who were admitted. In the event of diagnostic disagreement between the cardiology reviewers they were asked to meet to come to a common conclusion. In the event they were unable to come to a common conclusion, a third cardiology adjudicator was assigned by the endpoints committee to determine a final diagnosis. In order to come to a diagnosis of pneumonia, criteria modified from Fine et al 1990 and Leroy et al 1995 had to be fulfilled (Leroy et al. Intensive Care Med (1995) 21:24-31; Fine et al. Am J Med 1990; 89:713-721).

Measurement of Biomarkers

All blood samples were collected in EDTA-containing plastic tubes and plasma was stored at −70° C. in plastic freezer vials. PCT was measured with an automated sandwich chemiluminescence immunoassay on the KRYPTOR System (B.R.A.H.M.S AG, Hennigsdorf, Germany). The assay is based on the sandwich chemiluminescence assay which is described in detail elsewhere (Morgenthaler et al., Clin Chem 2002; 48:788-790).

Statistical Analysis

Values are expressed as means and standard deviations or counts and percentages as appropriate. Diagnostic groups were compared with independent-samples t-tests and chi-square tests as appropriate. Two primary objectives were evaluated using a p-value of 0.0125 as the significance criterion for each. All other analyses are exploratory and utilized a p-value of 0.05 for significance. The secondary analyses utilized logistic regression, Spearman's correlation, and ROC curve analysis. Outcome prediction was evaluated using Cox proportional hazard regression models. The predictive value of each model was assessed by the model likelihood ratio chi-square statistic. Survival curves plotted by the Kaplan-Meier method were used for illustrative purposes, and log-rank tests applied to test for survival differences.

Results

The 90-day-outcome in terms of survival was assessed for patients with shortness of breath that have been diagnosed with acute heart failure (AHF).

457 patients diagnosed with AHF had no treatment with antibiotics after entering the study, 104 were given antibiotics. 90 days after admission into the study, 46 of the patients not treated with antibiotics had died (10.1%). Of the patients treated with antibiotics, 18 patients had died until the $90^{th}$ day (17.3%).

Figure 2A:
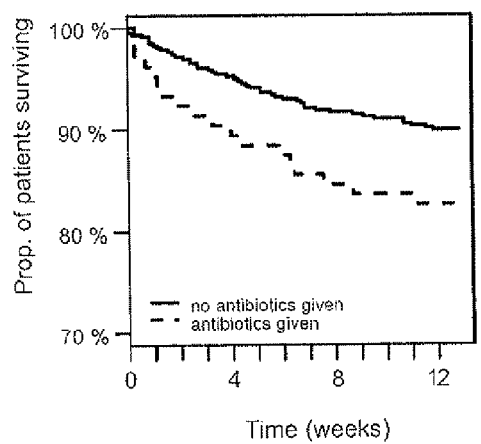
FIG. 2A-D.
Figure 2B:
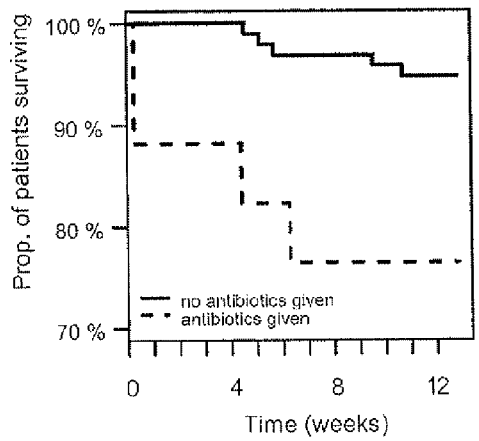
Figure 2C:
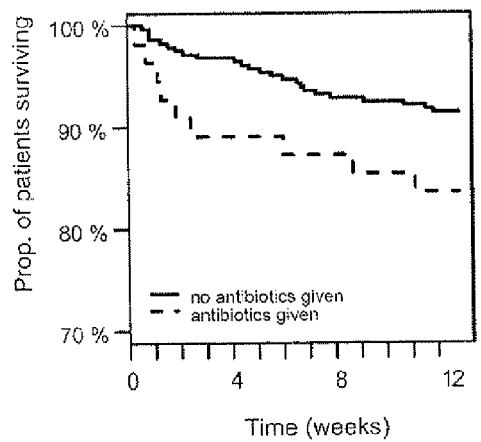
Figure 2D:
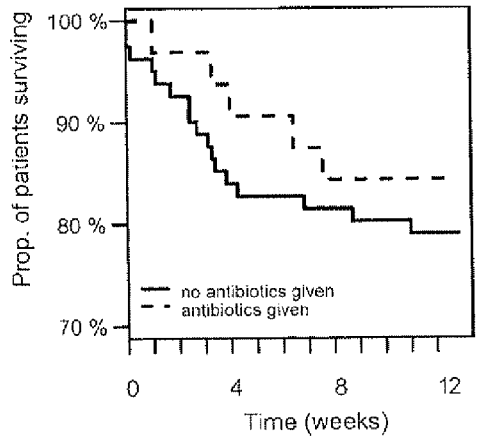
Figure 3A:
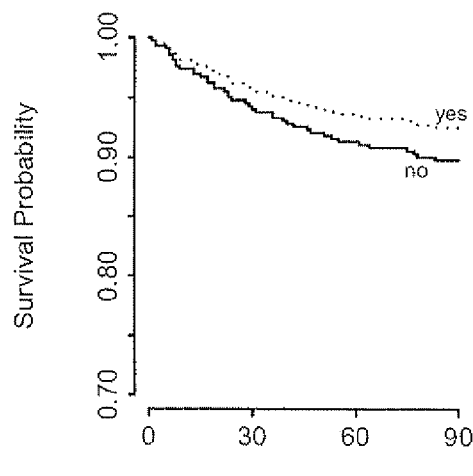
FIG. 3A-D.
Figure 3B:
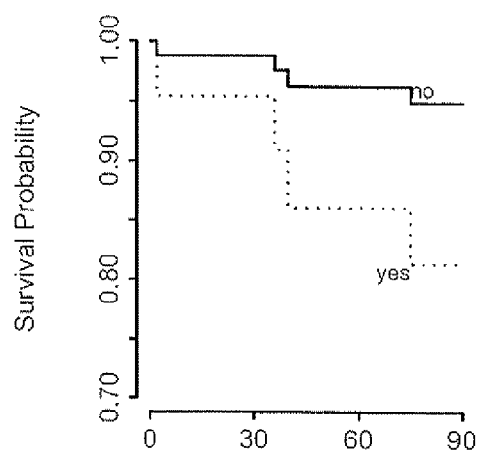
Figure 3C:
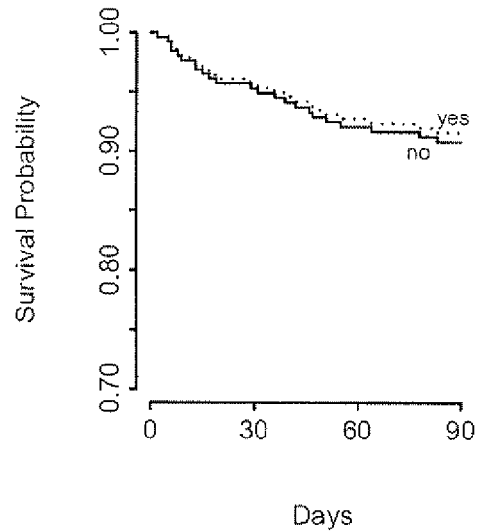
Figure 3D:
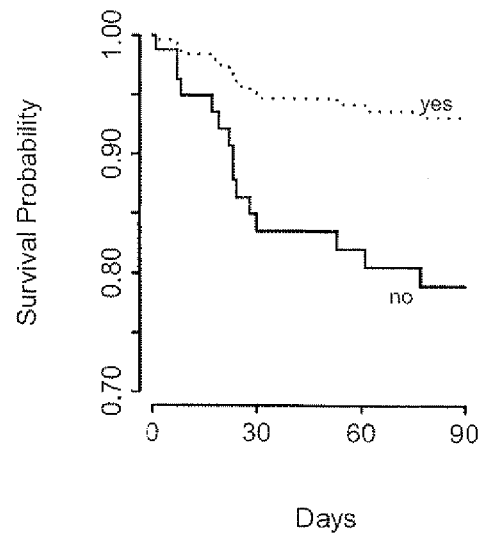

The outcome (survival rate) for patients diagnosed with AHF is illustrated in FIG. 2A-D. The group of patients without antibiotics treatment are indicated by solid lines, the group of patients with antibiotics treatment is indicated by dashed lines. FIG. 2A shows the outcome for patients independent of their plasma PCT level. FIG. 2B summarizes patients with plasma PCT levels of from 20.7 to 51.1 pg/mL (n=112), FIG. 2C summarizes patients with plasma PCT levels of from 51.1 to 205 pg/mL (n=336), FIG. 2D summarizes patients with plasma PCT levels of above 205 pg/mL (n=113). The results demonstrate that for patients with low PCT levels, i.e. below about 205 pg/mL and particularly below about 51.1 pg/mL the survival rate is lower in the group treated with antibiotics than in the non-treated group.

FIGS. 3A-D correspond to the respective FIGS. 2A-D except that the results have been adjusted for the covariants "occurrence of wheezing", "history of stroke" and "blood level of neutrophil granulozytes" in the patients to account for differences between the groups of antibiotics treated and non-treated patients. The results of FIG. 3 show that in patients with plasma PCT levels below about 51.1 pg/mL the mortality is higher in the antibiotics treated group of patients than in patients that have not been treated with antibiotics.

TABLE 1

Patient characteristics by diagnosis

| Variables | N | Non-AHF (N = 1073) | AHF (N = 568) | P |
|---|---|---|---|---|
| Demographics | | | | |
| Age | 1641 | 59.8 ± 17.0 | 71.2 ± 13.8 | <0.001 |
| Male Gender | 1641 | 504 (47.0) | 355 (62.5) | <0.001 |
| Race | 1626 | | | <0.001 |
| White | | 659 (62.1) | 431 (76.3) | |
| Black | | 356 (33.6) | 120 (21.2) | |
| Other | | 46 (4.3) | 14 (2.5) | |
| Recent History | | | | |
| Smoking | 1593 | 344 (33.0) | 125 (22.7) | <0.001 |
| Wheezing | 1543 | 359 (35.4) | 109 (20.6) | <0.001 |
| Weight Gain | 1438 | 112 (11.8) | 137 (28.0) | <0.001 |
| Night Sweats | 1495 | 230 (23.4) | 94 (18.3) | 0.025 |
| Orthopnea | 1536 | 349 (35.0) | 340 (63.0) | <0.001 |
| Dyspnea at Rest | 1605 | 518 (49.3) | 277 (49.9) | 0.834 |
| Exam Variables | | | | |
| Heart Rate | 1632 | 92.6 ± 21.6 | 89.2 ± 24.8 | 0.005 |
| Systolic BP | 1631 | 139.7 ± 26.8 | 143.0 ± 31.8 | 0.027 |
| Diastolic BP | 1630 | 79.6 ± 16.4 | 83.0 ± 18.7 | <0.001 |
| BMI | 1399 | 29.6 ± 9.1 | 28.5 ± 8.1 | 0.035 |
| Rales | 1624 | 216 (20.3) | 308 (54.8) | <0.001 |
| S3 | 1580 | 6 (0.6) | 38 (7.0) | <0.001 |
| Murmur | 1604 | 98 (9.3) | 156 (28.3) | <0.001 |
| JVP | 1539 | 71 (7.0) | 200 (38.2) | <0.001 |
| Edema | 1615 | 244 (23.1) | 344 (61.5) | <0.001 |
| Ascites | 1579 | 15 (1.5) | 26 (4.8) | <0.001 |
| Wheezing | 1619 | 350 (33.0) | 102 (18.2) | <0.001 |
| History Variables | | | | |
| Arrhythmia | 1555 | 168 (16.6) | 237 (43.6) | <0.001 |
| Asthma | 1594 | 288 (27.7) | 30 (5.4) | <0.001 |
| CRI | 1584 | 75 (7.2) | 171 (31.3) | <0.001 |
| HF | 1597 | 203 (19.6) | 366 (65.2) | <0.001 |
| CAD | 1587 | 232 (22.3) | 271 (49.5) | <0.001 |
| COPD | 1594 | 341 (32.7) | 130 (23.6) | <0.001 |
| DM | 1621 | 244 (23.1) | 218 (38.6) | <0.001 |
| Hyperlipidemia | 1549 | 330 (32.4) | 240 (45.3) | <0.001 |
| Hypertension | 1614 | 642 (60.9) | 438 (78.2) | <0.001 |
| MI | 1584 | 128 (12.3) | 172 (31.5) | <0.001 |
| Pulmonary Embolism | 1604 | 49 (4.7) | 36 (6.5) | 0.127 |
| CABG | 1615 | 66 (6.2) | 92 (16.5) | <0.001 |
| Angioplasty/Stent | 1602 | 96 (9.1) | 108 (19.6) | <0.001 |
| Stroke/CVA | 1608 | 89 (8.5) | 76 (13.7) | 0.001 |
| Pacemaker/ICD | 1616 | 55 (5.2) | 107 (19.1) | <0.001 |
| Prosthetic Valve | 1612 | 13 (1.2) | 30 (5.4) | <0.001 |

Notes:
Values are mean ± SD or N (%) and compared with independent samples t-test or Fisher exact tests, respectively.

The invention claimed is:

1. A method for diagnosing whether a subject suffering from a primary non-infectious disease has an increased risk of an adverse outcome potentially being induced by administration of an antibiotic to said subject, comprising:
   (a) detecting and quantifying in a sample of a bodily fluid from the subject the level of Procalcitonin (PCT) consisting of the amino acid sequence 2-116 or 3-116 of the PCT of SEQ ID NO:1, wherein said detection and quantitation comprises
      (i) contacting said sample with a diagnostic assay capture molecule which specifically binds to the PCT consisting of the amino acid sequence 2-116 or 3-116 to form a capture molecule:PCT complex and
      (ii) quantitating the capture molecule:PCT complex, and thereby determining the level of PCT in the sample;
   (b) comparing the thus-determined level of PCT in the sample with a predetermined value for diagnosing of whether the subject has an increased risk of an adverse outcome induced by the administration of an antibiotic, wherein the predetermined value indicates a statistically significant adverse outcome risk if the sample contains less than 200 pg/mL of PCT, whereby if the sample contains less than 200 pg/mL of PCT, said subject is diagnosed as having a statistically significant increased risk of having an adverse outcome induced by administration of an antibiotic, and whereby treatment with antibiotics is contraindicated, or if the prescribed treatment includes antibiotics, the subject is further monitored for symptoms of an adverse outcome, and
   wherein the sample of the bodily fluid of the subject is selected from the group consisting of: a blood sample, a serum sample, a plasma sample, a cerebrospinal fluid sample, a saliva sample, a urine sample and an extract of any of these samples.

2. The method of claim 1, wherein said outcome is an adverse event.

3. The method of claim 1, wherein said outcome is mortality.

4. The method of claim 1, wherein said subject has a primary non-infectious disease selected from the group consisting of cardiovascular disease, cardiac disease, cancer, a disease of the central nervous system, diabetes, autoimmune disorder, and a disorder associated with inflammation.

5. The method of claim 1, wherein said primary disease is congestive heart failure.

6. The method of claim 5, wherein said primary disease is acute heart failure.

7. The method of claim 5, wherein said primary disease is chronic heart failure.

8. The method of claim 1, wherein a concentration of PCT below 50 pg/mL in said sample correlates to an increased risk induced by the potential administration of an antibiotic.

9. The method of claim 1, whereby subjects suffering from a primary non-infectious disease are stratified into a group of subjects having an increased risk of an adverse outcome induced by the administration of an antibiotic and a group of subjects having no risk induced by the administration of an antibiotic.

10. The method of claim 2, wherein the adverse event is selected from the group consisting of a coronary event, cardiovascular event, death, heart failure, diabetes and hypertension.

11. The method of claim 10, wherein adverse event is a coronary event and the coronary event is a fatal or non-fatal acute myocardial infarction, or death due to ischemic heart disease.

12. The method of claim 10, wherein adverse event is a cardiovascular event and the cardiovascular event is a fatal or non-fatal acute myocardial infarction, fatal or non-fatal stroke, or death due to cardiovascular disease.

13. The method of claim 2, wherein the adverse event is a side effect induced by antibiotic treatment selected from upset stomach, diarrhea, a vaginal yeast infection, and an allergic reaction to the antibiotic.

14. The method of claim 1, wherein the capture molecule is an antibody.

15. The method of claim 1, wherein
   when the subject is determined to have a statistically significant risk of an adverse outcome, treatment which excludes administration of antibiotics is indicated, and
   when the subject is determined to not have a statistically significant risk of an adverse outcome, administration of antibiotics is indicated.

16. The method of claim 1, wherein the sample of the bodily fluid of the subject is selected from the group consisting of: a blood sample, a serum sample, a plasma sample, and an extract of any of these samples.

17. The method of claim 1, wherein the sample of the bodily fluid of the subject is a blood sample.

* * * * *

SEQUENCE LISTING

<160> NUMBER OF SEQ ID NOS: 1

<210> SEQ ID NO 1
<211> LENGTH: 116
<212> TYPE: PRT
<213> ORGANISM: Homo sapiens

<400> SEQUENCE: 1

```
Ala Pro Phe Arg Ser Ala Leu Glu Ser Ser Pro Ala Asp Pro Ala Thr
1               5                   10                  15
```

-continued

```
Leu Ser Glu Asp Glu Ala Arg Leu Leu Leu Ala Ala Leu Val Gln Asp
            20                  25                  30

Tyr Val Gln Met Lys Ala Ser Glu Leu Glu Gln Glu Gln Glu Arg Glu
            35                  40                  45

Gly Ser Ser Leu Asp Ser Pro Arg Ser Lys Arg Cys Gly Asn Leu Ser
        50                  55                  60

Thr Cys Met Leu Gly Thr Tyr Thr Gln Asp Phe Asn Lys Phe His Thr
65                      70                  75                  80

Phe Pro Gln Thr Ala Ile Gly Val Gly Ala Pro Gly Lys Lys Arg Asp
                85                  90                  95

Met Ser Ser Asp Leu Glu Arg Asp His Arg Pro His Val Ser Met Pro
                100                 105                 110

Gln Asn Ala Asn
            115
```